(12) United States Patent
Andersen et al.

(10) Patent No.: US 7,261,706 B2
(45) Date of Patent: Aug. 28, 2007

(54) PACKAGE FOR AN OSTOMY APPLIANCE

(75) Inventors: Birthe Vestbo Andersen, Espergaerde (DK); Eskil Hoelland Olsen, Humlebaek (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 10/488,864

(22) PCT Filed: Sep. 6, 2002

(86) PCT No.: PCT/DK02/00586

§ 371 (c)(1),
(2), (4) Date: Oct. 8, 2004

(87) PCT Pub. No.: WO03/022186

PCT Pub. Date: Mar. 20, 2003

(65) Prior Publication Data

US 2005/0040060 A1    Feb. 24, 2005

(30) Foreign Application Priority Data

Sep. 7, 2001    (DK) ................ 2001 01320

(51) Int. Cl.
A61M 1/00    (2006.01)
(52) U.S. Cl. ....................... 604/322; 604/317
(58) Field of Classification Search ............... 604/322, 604/317; 383/35; 206/363
See application file for complete search history.

(56) References Cited

U.S. PATENT DOCUMENTS

| 1,211,025 | A | * | 1/1917 | Wright .................. 150/149 |
| 3,096,013 | A | * | 7/1963 | Kugler .................. 383/119 |
| 3,553,331 | A | * | 1/1971 | Kugler .................. 514/659 |
| 3,558,406 | A | * | 1/1971 | Kugler .................. 156/515 |
| 3,596,828 | A | * | 8/1971 | Foster et al. .................. 383/94 |
| 3,680,768 | A | * | 8/1972 | Warren .................. 383/40 |
| 4,065,344 | A | * | 12/1977 | Weist .................. 156/250 |
| 4,256,256 | A | * | 3/1981 | Meyers .................. 383/40 |
| 4,679,688 | A | * | 7/1987 | Soderholm et al. .......... 206/204 |
| 4,744,673 | A | * | 5/1988 | Nakamura .................. 383/38 |
| 5,024,536 | A | * | 6/1991 | Hill .................. 383/38 |
| 5,082,006 | A |   | 1/1992 | Jonasson |
| 5,135,519 | A |   | 8/1992 | Helmer |
| 5,647,670 | A |   | 7/1997 | Iscovich |
| 5,778,110 | A | * | 7/1998 | Furuya .................. 383/35 |
| 5,860,774 | A | * | 1/1999 | Teper .................. 408/108 |
| 6,153,232 | A | * | 11/2000 | Holten et al. .................. 426/79 |
| 6,186,663 | B1 | * | 2/2001 | Ausnit .................. 383/63 |
| 2004/0179754 | A1 | * | 9/2004 | Taheri .................. 383/38 |

FOREIGN PATENT DOCUMENTS

| DE | 30 38923 | 5/1982 |
| DE | 296 20 464 | 3/1997 |
| DE | 297 03 223 | 5/1997 |
| FR | 2 638 426 | 5/1990 |
| GB | 2 083 762 | 3/1982 |
| HU | 52939 | 9/1990 |
| WO | 93/09743 | 5/1993 |
| WO | 94/14396 | 7/1994 |

* cited by examiner

Primary Examiner—Tatyana Zalukaeva
Assistant Examiner—Ginger Chapman
(74) Attorney, Agent, or Firm—Jacobson Holman PLLC

(57) ABSTRACT

A package for a disposable ostomy receiving bag, the package including a first compartment capable of accommodating a fresh ostomy receiving bag and a second compartment capable of accommodating a used ostomy receiving bag. The second compartment is sealable so as to confine the receiving bag which facilitates the handling of fresh and used bags and renders the user more independent of the availability of a lavatory.

20 Claims, 5 Drawing Sheets

PACKAGE FOR AN OSTOMY APPLIANCE

This is a nationalization of PCT/DK02/00586 filed Sep. 6, 2002 and published in English.

BACKGROUND OF THE INVENTION

FIELD OF THE INVENTION

The present invention relates to a package for a collecting bag to be secured to the abdomen of a patient or to a body side ostomy member for collecting fluids or excretions emerging from an abdominal stoma.

In connection with surgery for a number of diseases in the gastro-intestnal or urinary tract a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening.

Ostomy appliances are well known. Such appliances may be two-piece or one-piece appliances. In both types of appliances, an adhesive barrier member (or base plate) is attached to the wearer's abdomen/back/chest. In case of a one-piece appliance, a receiving member or bag is attached to the base plate. In case of a two-piece appliance, the adhesive barrier member forms part of a body side member and a receiving member or bag is attached releasably to the body side ostomy member for receiving exudates from the stoma.

When using one-piece appliances, the whole appliance, including the adhesive skin barrier securing the appliance to the skin is normally removed and replaced by a fresh appliance. When using two-piece appliances, the body side ostomy member is left in place up to several days, and only the receiving member or bag attached to the body side member is replaced. The attachment means for attaching an ostomy receiving bag may e.g. be a system comprising matching coupling rings or matching flanges and adhesive surfaces engaging with and sealing against a flange area of the body side member.

A known major problem with such receiving bags is that it can be difficult to dispose of the used bag in a convenient and hygienic manner. Some ostomists will cut the used bags open, e.g. by cutting off an edge thereof and deposit the contents into a WC for flushing away and dispose or deposit the empty bag in a waste bin. Such disposal of used bags and the contents therein is indeed unhygienic and unpleasant for the user, and the problems with disposal of a used bag is even more pronounced if the user does not have access to normal toilet facilities, e.g. when travelling.

SUMMARY OF THE INVENTION

The present invention relates to a package for a disposable ostomy receiving bag.

The present invention is described with reference to use in connection with an ostomy collecting bag but other uses of the package overcoming corresponding problems are also considered a part of the invention, e.g. the use in connection with handling hygienic articles such as sanitary towels or diapers.

BRIEF DESCRIPTION OF THE DRAWINGS

The invention is disclosed more in detail with reference to the drawings in which.

DETAILED DESCRIPTION OF THE PRESENT INVENTION

Figure 1:
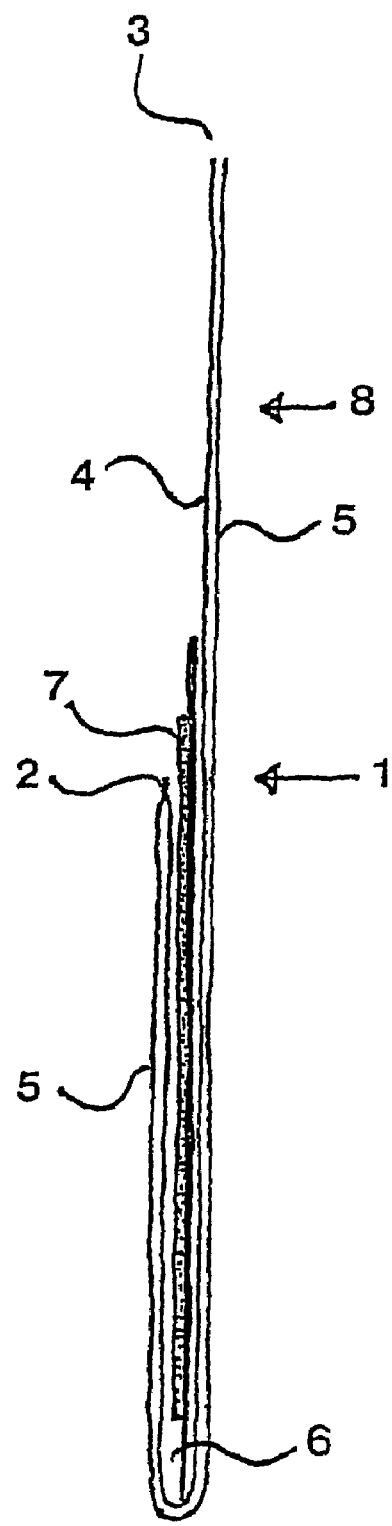
FIG. 1 shows a sectional view of an embodiment of package of the invention showing an open first compartment.

The present invention relates to a package for a disposable ostomy receiving bag, said package comprising a first compartment capable of accommodating a (fresh) ostomy receiving bag and a second compartment capable of accommodating a used ostomy receiving bag, said second compartment being sealable so as to confine the receiving bag.

The bag of the invention facilitates the handling of fresh and used bags and renders the user more independent on immediate availability of a lavatory or toilet facilities when having to substitute a bag while being out of the daily whereabouts. Thus, the invention renders it easy for an ostomate to carry a fresh bag in a discrete manner and also to handle the used bag in a safe and discrete manner reducing the risk of embarrassing situations in case of a leak liberating odour or the contents of the bag. This will increase the chances of living a more normal social life and increase the quality of life of the ostomate.

The package of the invention may be used for receiving bags for both one-piece and two-piece applications.

Suitable materials for a package of the present invention are thin flexible sheet materials which are moisture resistant and impervious to liquids and preferably also odours, e.g. polyolefins such as polyethylene or polypropylene, EVA, polyvinylidene chloride, or chlorinated polyethylene or copolymers of PE and EVA or combinations of such foils. The walls of the bag may in a special embodiment be laminated with materials conventionally used in the production of ostomy appliances such as non-woven materials of polyethylene, polypropylene or a polyester.

A suitable embodiment of a package is in the form of a bag having a closed end and an open end and having a first wall and a second wall, said bag being folded so that the closed end of the first wall is parallel to the open end of the first wall and the edges of the folded first wall being sealed releasably together to form the first compartment. In this embodiment, a relatively large bag which may accommodate a used bag with contents is also rendered suitable for accommodating a fresh receiving bag and, at the same time, ensures as high a degree of discretion as it may e.g. be carried in a hand bag or a pocket. It is preferred that the material for a package of the invention is opaque for blurring the contents for improving the discretion when it is necessary to carry the package containing a used bag.

The sealing may be effected using adhesive or a peel welding seam known per se, said seam preferably stretching along the rims of the folded bag. The seams may be continuous or interrupted. The peel strength of adhesive or welding seam should preferably be lower than the tearing resistance of the material for the package for enabling an easy breaking of the seal without risk of damaging the walls of the bag compromising the later use for carrying the used bag.

It is preferred that the closed end of the bag, in its folded position, leaves a part of the open end of the bag free as a flap capable of covering the inlet opening of the compartment as this flap will protect a fresh bag against mechanical damage when stowed in a hand bag or a pocket.

In accordance with another preferred embodiment, one of the walls of the open end of the bag (the one being at the outside after folding the bag) is extended beyond the edge of the other wall forming an extended flap which may have a general rectangular, triangular or oval shape or the shape of a part of a circle.

The safety against damage and unintended catching of the bag is increased when the flap and the outer surface of the second wall forming the first compartment are provided with means for releasable attachment of the flap to the surface of the wall. Such means may be a releasable adhesive sealing or a peelable weld seam. The sealing may alternatively be effected using an adhesive label placed on the flap. Such a label may also be used in a manner known per se for carrying information identifying the product.

It is preferred that the package is in the form of a bag made from a tube of a thermoplastic material, flattening the same and, optionally folding the edges at the same time to make two longitudinal folds (in analogy with conventional production of plastics bags) and in a subsequent step cutting the tubing into the desired length and, preferably at the same time welding the bottom part thereof to form a bag. The bag may then be folded and the overlying edges sealed by applying an adhesive seal or a welding seam in a manner known per se. This embodiment enables an expansion of the bag to have a larger opening enabling a safer placing of the used ostomy receiving bag without risk of soiling the sides of the open end of the bag which might compromise a safe containment and very low risk of escape of odour.

In a more preferred embodiment, the package is in the form of a bag made from a sheet of a thermoplastic material by folding the sheet and welding the aligned edges forming a bag. Then, the bag may then be folded and the overlying edges sealed by applying an adhesive seal or a welding seam in a manner known per se. This embodiment provides a bag having edges having a welding seam and hence, a greater tearing resistance giving a more free choice of selecting the adhesive material or the welding conditions when folding and sealing the edges of the first wall of the bag to form the first compartment.

A safe and discrete depositing of the used bag when having to rely on using a waste bin is secured when the bag is made from a material being substantially impervious to odour. A suitable such material is a material conventionally being used for production of ostomy appliances, e.g. the ones mentioned above.

DESCRIPTION OF THE PREFERRED EMBODIMENTS

The invention is now explained more in detail with reference to the drawings showing preferred embodiments of the invention. However, it should be understood that the detailed description and specific examples, while indicating preferred embodiments of the invention, are given by way of illustration only, since various changes and modifications within the spirit and scope of the invention will become apparent to those skilled in the art from this detailed description.

Reference is made to FIG. 1 showing a sectional view of a preferred embodiment of a package of the invention in the form of a bag 1 having a closed end 2 and an open end 3 and having a first wall 4 and a second wall 5, said bag being folded so that the closed end of the first wall is parallel to the open end of the first wall and the edges of the folded first wall being sealed releasably together to form the first compartment 6. In the first compartment is shown an ostomy collecting bag 7. The open end 3 of the bag stretches beyond the folded closed end forming a flap 8.

Figure 2:
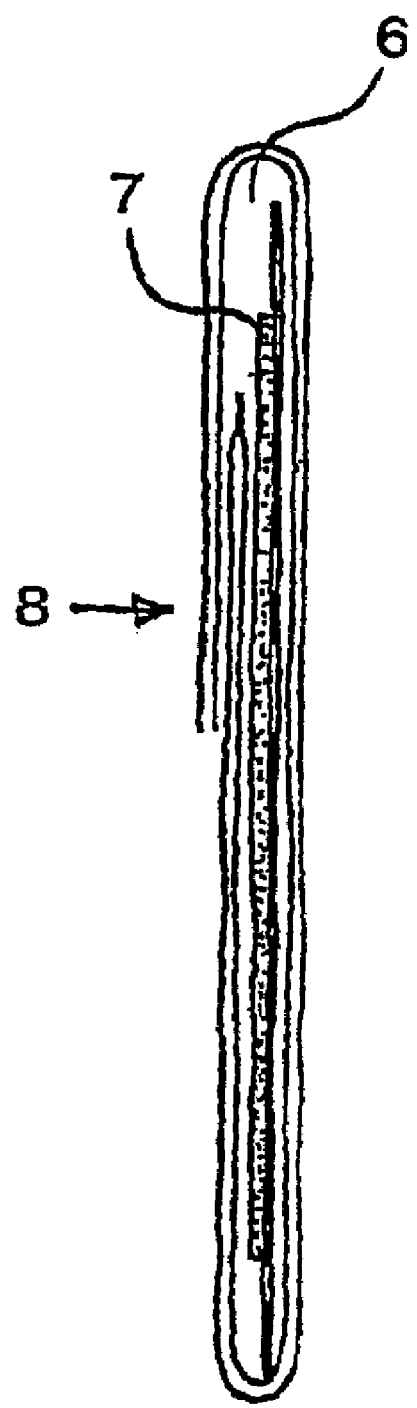
FIG. 2 shows the same embodiment as FIG. 1 having a closed first compartment.

In FIG. 2 shows the embodiment as FIG. 1 having a first compartment 6 closed by folding the flap 8 so that the first wall 4 contacts the outer surface of the second wall 5, said compartment encasing the ostomy receiving bag 7.

Figure 3:
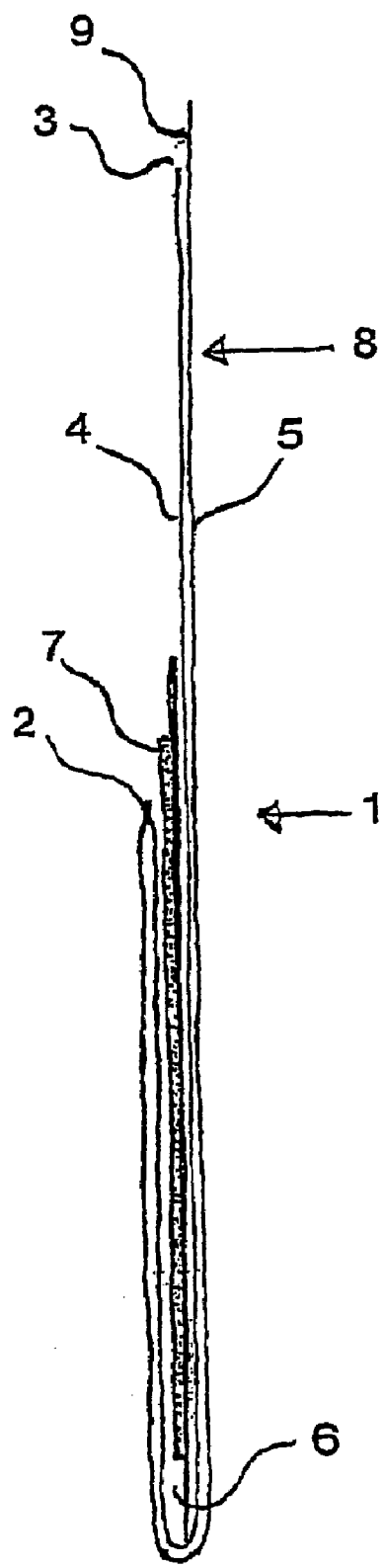
FIG. 3 shows another embodiment of a package of the invention.

FIG. 3 shows a sectional view of an embodiment of a package of the invention in the form of a bag 1 having a closed end 2 and an open end 3 and having a first wall 4 and a second wall 5, said bag being folded so that the closed end of the first wall is parallel to the open end of the first wall and the folded edges of the first wall being sealed releasably together to form the first compartment 6. In the first compartment is shown an ostomy collecting bag 7. The open end 3 of the bag stretches beyond the folded closed end forming a flap 8, the wall 5 being extended beyond the edge of the other wall forming an extended flap 9.

Figure 4:
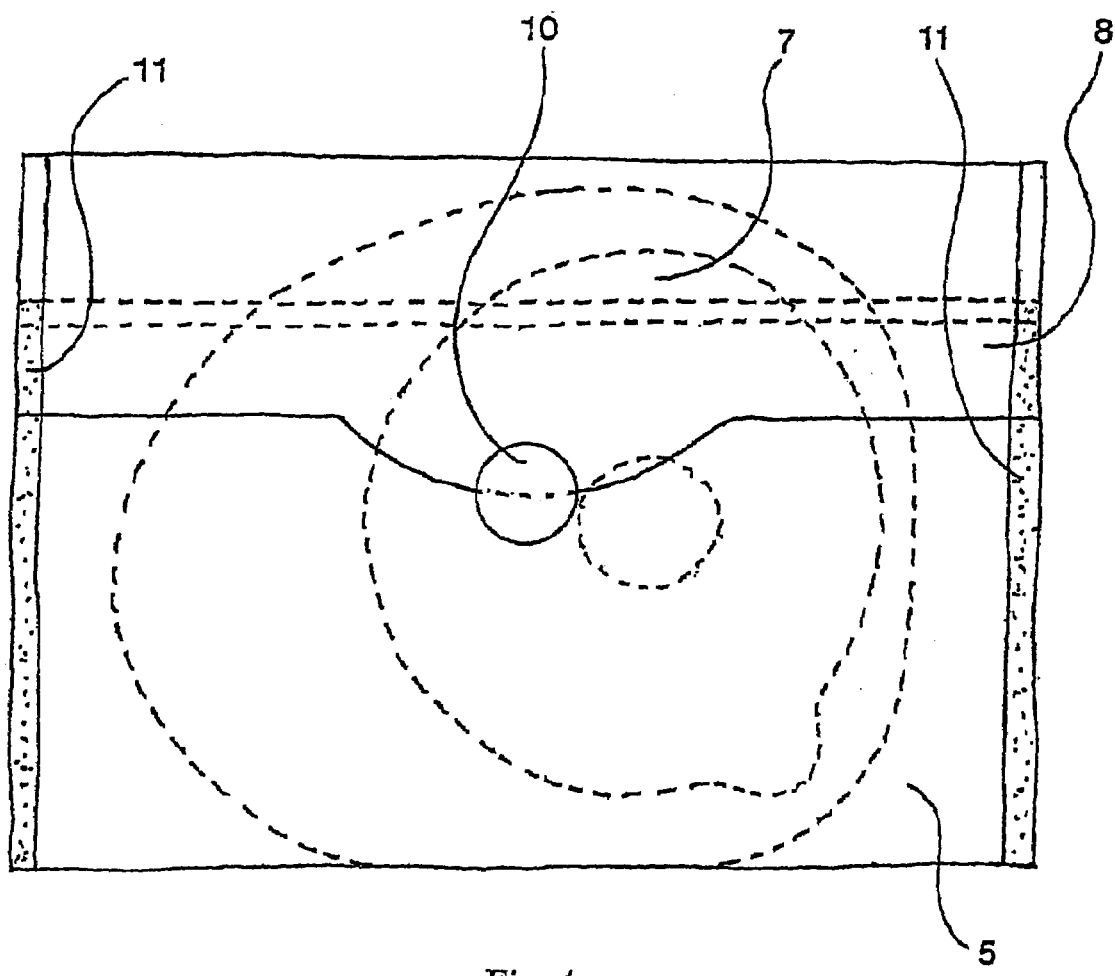
FIG. 4 shows a front view of a closed package of the invention.

FIG. 4 shows a front view of an embodiment of a package of the invention having a first compartment closed by folding the flap 8 so that the first wall contacts the outer surface of the second wall 5, said compartment encasing an indicated ostomy receiving bag 7, the outer surface of the second wall and further being provided with an adhesive label 10 for closing the first compartment. Furthermore, the edges of the folded two parts of the first wall are sealed releasably by welding seams 11.

Figure 5:
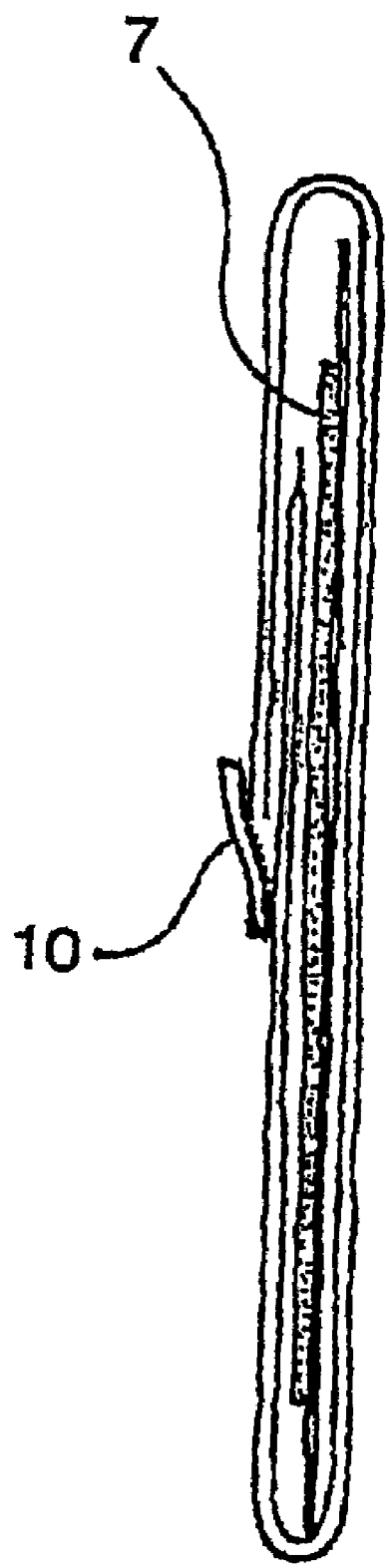
FIG. 5 shows a sectional view of the package shown in FIG. 4.

FIG. 5 shows a sectional view of the embodiment of FIG. 4. This embodiment corresponds to the embodiment of FIG. 2 apart from the presence of the adhesive label 10.

When using the package of the invention, the ostomate breaks the seal of the flap, opens the first compartment and removes the fresh ostomy receiving bag for substituting the one in use. Then, the sealings closing the first compartment by sealing the edges of the folded first wall together are broken enabling an unfolding of the bag and give access to the full space of the package forming the second compartment. After detaching the used receiving bag from the abdomen or from an ostomy body side member, the bag may be placed in the second compartment with or without emptying the bag as is appropriate. Then the package is advantageously sealed by tying a knot on a part of the open end or using another suitable sealing means such as a clamp known per se for sealing an ostomy bag or an adhesive sealing which is preferably covered by a protecting release liner made from a suitable material such as polyethylene or a siliconised paper to be removed before use or a reusable adhesive placed on the flap. When a reusable adhesive is used on the flap, this may also be used for closing the second compartment in which the used receiving bag is then safely confined.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A package for a disposable ostomy receiving bag, said package comprising a first wall and a second wall in the form of a bag made of a flexible sheet material that is impervious to liquids, said bag extending a length of said first and second walls and having a closed end and an open end that define a sealable compartment configured to receive and confine a used ostomy receiving bag along with its contents to prevent leakage of said contents from said compartment, said bag with said compartment being folded upon itself such that the closed end is brought nearer to the open end to form an inlet opening and a lower portion of the first wall lies adjacent an upper portion of said first wall, side edges of the upper and lower portions of the folded first wall being releasably sealed together to form an additional compartment bounded by the adjacent portions of said first wall, said releasably sealed side edges and said fold, said additional compartment configured to carry a fresh ostomy receiving bag received through said inlet opening.

2. The package as claimed in claim 1 wherein release of said releasably sealed edges allows unfolding of said bag for insertion of the used ostomy receiving bag in said compartment.

3. The package as claimed in claim 1 wherein when said bag is unfolded and a used ostomy receiving bag is placed in said compartment, said open end is configured to be sealed by tying said open end in a knot to contain odors and liquid contents of said ostomy receiving bag within said compartment with said bag in an unfolded orientation.

4. The package as claimed in claim 1 wherein said additional compartment is eliminated when said bag is unfolded.

5. The package as claimed in claim 1 wherein said compartment is formed without folding.

6. The package as claimed in claim 1 wherein the closed end of the bag, in its folded position, leaves a part of the open end of said bag free as a flap capable of covering at least one of the inlet opening of said additional compartment and the open end of said compartment.

7. The package as claimed in claim 6 wherein the flap and an outer surface of the second wall, as folded with the lower portion of said first wall to form the additional compartment, are provided with a releasable attachment component to attach the flap to said outer surface.

8. The package as claimed in claim 1 wherein the package is made from a material that is substantially impervious to odor.

9. The package as claimed in claim 1 wherein an overall length of said compartment prior to folding is over twice a depth of said additional compartment when said bag is folded.

10. The package as claimed in claim 1 wherein said flexible sheet material is a thermoplastic material.

11. The package as claimed in claim 1 wherein said releasably sealed side edges include an adhesive or peel welding seam having a peel strength that is lower than a tearing resistance of said bag for enabling a breaking of the sealed side edges without damage to the bag.

12. A package for a disposable ostomy receiving bag, said package comprising a first wall and a second wall made of a flexible sheet material that is impervious to liquids and joined at respective bottoms thereof to form a closed end, with an end opposite said closed end being open so that a containment bag extending a length of said first and second walls is formed, said containment bag being folded between said closed end and said open end so that the closed end is substantially parallel to the open end and a lower portion of the first wall is brought adjacent an upper portion of said first wall to form an inlet opening, side edges of the upper and lower portions of the folded first wall being releasably sealed together to form a first compartment bounded by said releasably sealed edges and said fold, said first compartment capable of carrying a fresh ostomy receiving bag received through said inlet opening, release of said releasably sealed edges allowing longitudinal extension of said containment bag to define a second compartment between said first and second walls and said closed end, said second compartment configured to receive a used ostomy receiving bag through said open end and be sealed so as to confine the used receiving bag and prevent leakage of its odors and content including liquids from said second compartment.

13. The package as claimed in claim 12 wherein the closed end of the containment bag, in its folded position, leaves a part of the open end of said containment bag free as a flap capable of covering at least one of the inlet opening of said first compartment and the open end of said second compartment.

14. The package as claimed in claim 13 wherein the flap and an outer surface of the second wall forming the first compartment are provided with a releasable attachment element to attach the flap to said outer surface.

15. The package as claimed in claim 12 wherein the length of said containment bag is over twice a depth of said first compartment.

16. The package as claimed in claim 12 wherein said flexible sheet material is a thermoplastic material.

17. The package as claimed in claim 12 wherein said releasably sealed side edges include an adhesive or peel welding seam having a peel strength that is lower than a tearing resistance of said bag for enabling a breaking of the sealed side edges without damage to the bag.

18. A package for a disposable ostomy receiving bag, said package comprising a bag made of a flexible thermoplastic material having a closed end and an open end that define a sealable compartment capable of receiving and confining a used ostomy receiving bag and configured to prevent leakage of bag contents including liquids from said compartment, said bag with said compartment being folded upon itself such that the closed end is brought nearer to the open end to form an inlet opening and an inside wall, side edges of the inside wall as formed by the folding being releasably sealed together to form an additional compartment bounded by the inside wall, said releasably sealed side edges and said fold and capable of carrying a fresh ostomy receiving bag received through said inlet opening.

19. The package as claimed in claim 18 wherein said releasably sealed side edges include an adhesive or peel welding seam having a peel strength that is lower than a tearing resistance of said thermoplastic material for enabling a breaking of the sealed side edges without damage to the bag.

20. The package as claimed in claim 18 wherein a length and width of said sealable compartment substantially corresponds with a respective length and width of said bag when unfolded.

* * * * *